United States Patent
Subbarao

(10) Patent No.: US 8,008,625 B2
(45) Date of Patent: Aug. 30, 2011

(54) METHOD AND APPARATUS FOR HIGH-SENSITIVITY SINGLE-PHOTON EMISSION COMPUTED TOMOGRAPHY

(76) Inventor: Muralidhara Subbarao, Stony Brook, NY (US)

( * ) Notice: Subject to any disclaimer, the term of this patent is extended or adjusted under 35 U.S.C. 154(b) by 18 days.

(21) Appl. No.: 12/586,863

(22) Filed: Sep. 29, 2009

(65) Prior Publication Data

US 2011/0073763 A1    Mar. 31, 2011

Related U.S. Application Data

(60) Provisional application No. 61/276,570, filed on Sep. 14, 2009.

(51) Int. Cl.
*G01T 1/10* (2006.01)
(52) U.S. Cl. .................................................. 250/362
(58) Field of Classification Search ............... 250/362, 250/363.01–363.1
See application file for complete search history.

(56) References Cited

U.S. PATENT DOCUMENTS

| | | | |
|---|---|---|---|
| 5,462,056 A | | 10/1995 | Hawman et al. |
| 5,565,684 A | | 10/1996 | Gulberg et al. |
| 5,591,977 A | * | 1/1997 | Green et al. ............. 250/363.03 |
| 5,717,212 A | * | 2/1998 | Fulton et al. ............. 250/363.05 |
| 6,194,728 B1 | * | 2/2001 | Bosnjakovic ............ 250/370.11 |
| 7,521,681 B2 | | 4/2009 | Hawman |
| 7,558,709 B2 | | 7/2009 | Subbarao |
| 7,577,309 B2 | | 8/2009 | Subbarao |
| 2010/0001190 A1 | * | 1/2010 | Wieczorek et al. ........... 250/362 |
| 2010/0163736 A1 | * | 7/2010 | Ohana et al. .................. 250/362 |
| 2010/0204563 A1 | * | 8/2010 | Stodilka et al. ............... 600/411 |

OTHER PUBLICATIONS

Book: A. C. Kak and M. Slaney, Principles of Computerized Tomographic Imaging, Society of Industrial and Applied Mathematics, 2001. ISBN-10: 089871494X, Chapter 3, pp. 49-112.

* cited by examiner

*Primary Examiner* — Kiho Kim

(57) ABSTRACT

A method and apparatus are disclosed for high-sensitivity Single-Photon Emission Computed Tomography (SPECT), and Positron Emission Tomography (PET). The apparatus includes a two-dimensional (2D) gamma detector array that moves to different positions in a three-dimensional (3D) volume space near an emission source and records a data vector g. In particular, the 3D volume space in which emission data g is measured extends substantially along a radial direction r pointing away from the emission source and each photon detector element in the 2D gamma detector array is provided with a very large collimator aperture. Data g is related to the 3D spatial density distribution f of the emission source, noise vector n, and a system matrix H of the SPECT/PET apparatus through the linear system of equations g=Hf+n. This equation is solved for f by a method that reduces the effect of noise.

10 Claims, 6 Drawing Sheets

Figure 1:
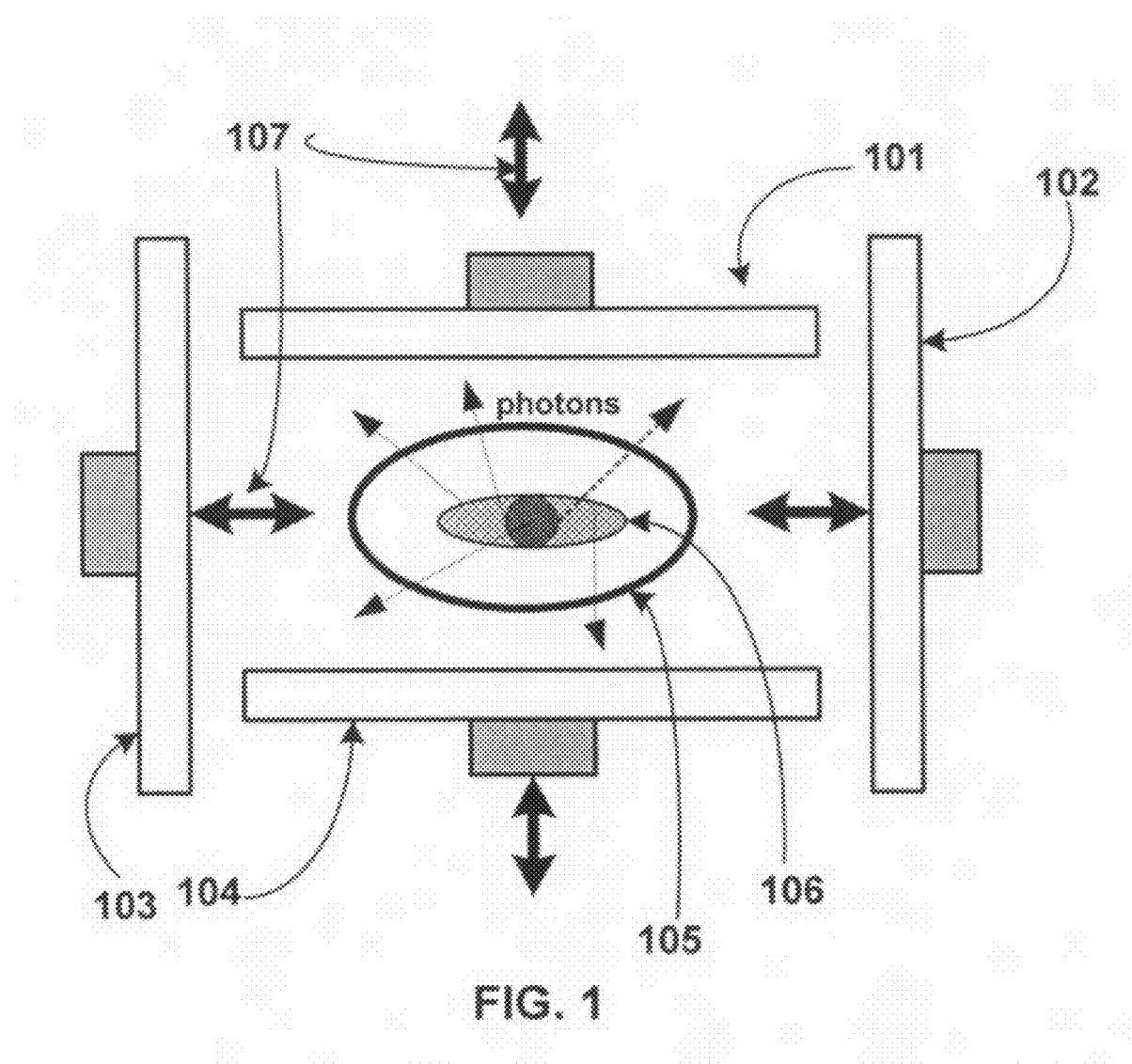

Using one or more 2D planar gamma detector arrays that move or rotate to different positions in 3D space, measure Gamma emission intensity data denoted by g=g(x',y',z') in a 3D volume space V that extends substantially along the radial dimension pointing away from an approximate center of a gamma emission source inside a body. This may be done using a novel SPECT apparatus shown in FIG. 1 or FIG. 2 or any suitable apparatus.

⬇

Measure the linear attenuation matrix $\mu$(x,y,z) of the body material for each voxel at (x,y,z) in a volume P through which the gamma emission from the source in the body passes through before being detected by the gamma detector. MRI or X-ray CT may be used.

⬇

Compute path attenuation coefficient matrix C = c(x',y',z',x,y,z) that gives the attenuation of an emission ray going from point (x,y,z) to the sensor detector at (x',y',z'). This computation is made using $\mu$(x,y,z).

⬇

Use the precomputed matrices $\theta$(x',y',z',x,y,z) which gives the angle between a ray going from (x,y,z) to (x',y',z') and the surface normal vector n of the sensor element at (x',y',z') when the measurement g(x',y',z') is made, and the aperture geometry matrix a(x',y',z',x,y,z) that gives attenuation of radiation measured at (x',y',z') of radiation from volume element at (x,y,z). Use these matrices, the path attenuation coefficient matrix C, and the radiation propagation property, to compute the system matrix H(x',y',z',x,y,z) and formulate the equation $$g(x',y',z') = \sum_x \sum_y \sum_z H(x',y',z',x,y,z) f(x,y,z) + n(x',y',z')$$

$$\mathbf{g} = \mathbf{Hf} + \mathbf{n}$$

⬇

Solve the equation g=Hf+n for the desired quantity f by a method that reduces the effect of noise n significantly so that the desired goal of determining the spatial density distribution f of the radiation emission source is achieved. Expectation maximization, regularization based on spectral filtering, etc. are some of the methods that reduce the effect of noise n.

FIG. 7 Method of the Invention

METHOD AND APPARATUS FOR HIGH-SENSITIVITY SINGLE-PHOTON EMISSION COMPUTED TOMOGRAPHY

DESCRIPTION

This patent application is a continuation of the following U.S. Provisional Patent Application filed by this inventor:

M. Subbarao, "Method and Apparatus for High-Sensitivity Single-Photon Emission Computed Tomography (SPECT)", U.S. Provisional Patent Application No. 61/276,570, filed on Sep. 14, 2009.

This patent application provides details of the description of the above invention.

1. FIELD OF THE INVENTION

The present invention relates to a method and apparatus for Single Photon Emission Computed Tomography (SPECT) in Nuclear Medicine. This method and apparatus are also applicable to Positron Emission Tomography (PET). The method and apparatus are specifically related to exploiting the information in the spatial intensity distribution of the three-dimensional (3D) photon emission field in a 3D volume space around an emission source. This information can reveal the 3D spatial density distribution of the emission source. In particular, the 3D volume space is designed to extend substantially along the radial distance pointing away from the emission source in order to obtain reliable results due to the inevitable presence of noise in measurements. The method and apparatus permit the use of very large collimator apertures, including the maximum possible of up to 180 degrees field-of-view, and therefore provide a very high-sensitivity SPECT/PET method and apparatus with the advantages of lower radiation dosage for patients, lower cost of procedure, and faster procedure.

2. BACKGROUND OF THE INVENTION

Medical radionuclide imaging or nuclear medicine is an important diagnostic tool for obtaining three-dimensional (3D) maps of the distribution of a radiation emission source administered to a patient. SPECT is a commonly used radionuclide imaging technique. Gamma radiation detectors are used to record the emission from the patient's body. This recorded data is used to reconstruct the 3D spatial distribution of the emission source in the patient's body. This reconstructed image is useful in the diagnosis of problems in different organs such as kidney, blood-vessels, heart, lungs, bone, and brain.

SPECT machines in prior art have relatively low sensitivity because they use a small aperture or small field-of-view collimator for gamma detectors. About 99% or more of the gamma photons carrying useful information are blocked and wasted by these small aperture/field-of-view collimators. As a result, Signal-to-Noise ratio in the gamma emission measurements are very low leading to poor quality in reconstructed tomographic images. Large field of view collimators are not used as they result in highly blurred images with depth/distance dependent blur of the radiation emission source and reduce the spatial resolution of reconstructed tomographic images. Large collimator apertures also increase errors due to increase in the sensing of scattered gamma rays which make the reconstructed tomographic images less accurate. These limitations of using a large aperture collimators are prevalent in the SPECT methods and apparatus in prior art but they are not as much in the novel SPECT method and apparatus disclosed here.

The theoretical foundation of the conventional SPECT method and apparatus is based on the following theoretical result: the tomographic reconstruction that provides the 3D spatial density distribution of a gamma emission source can be made from beam projection data, i.e. the measured values of the line-integral of the density of gamma emission source along different directions of view. Fourier-slice theorem states this result nicely for parallel projection data. See page 56 in the following book which is sold in book shops as well as freely available at www.slaney.org/pct:

A. C. Kak and Malcolm Slaney, *Principles of Computerized Tomographic Imaging*, Society of Industrial and Applied Mathematics, 2001. ISBN-10: 089871494X.

In practice, integral/sum of the attenuated intensity of emission source elements along a thin line is measured. The thickness and shape of the elements' along the thin line in 3D space are determined by the collimator geometry, specifically the small aperture/field-of-view of the collimator. Attenuation of the emission is caused by the material substance around the emission source and through which the emission passes through before being measured. The measured line-integrals are called projection data or sinogram of attenuated emission. Projection data corresponding to different collimator structures such as parallel/converging/diverging-hole, fan-beam, cone-beam, etc., are used in prior art. However, all of this prior art is based on this theory of measuring and inverting line-integrals. When it becomes necessary to increase signal-to-noise ratio, i.e. increase sensitivity to information-carrying (non-scattered) gamma rays, the use of large apertures are forced by the rules of physics and geometry, and are accepted and used reluctantly. The distance/depth-dependent image blur of emission source caused by large apertures is treated as a serious undesirable problem. This depth dependent blur is reduced through one of several techniques that trade-off spatial resolution for errors due to noise in the reconstructed tomographic image. The gamma emission field is typically measured on a 2D planar surface that rotates around the emission source at a roughly constant/fixed distance/radius from an approximate center point of the emission source (see FIG. 3). The set of all points at which the emission field is measured forms a 3D surface with a small volume in the shape of a thin annular cylinder. In particular, this volume extends by a very small length along the radial dimension, but extends substantially much more along directions perpendicular to the radial distance.

A good description of conventional SPECT apparatus and method can be found in

1. P. C. Hawman, J. Qian; J. D. Treffert, "High-sensitivity SPECT imaging of small body organs using a multi-headscintillation camera with non-uniform collimation", U.S. Pat. No. 5,462,056, Oct. 31, 1995.
2. G. T. Gulberg and G. L Zeng, "Three-dimensional SPECT reconstruction of combined cone-beam and fan-beam data", U.S. Pat. No. 5,565,684, Oct. 15, 1996.

A more recent development on a SPECT apparatus with a specially designed collimator structure that does not involve relative rotation between a patient and a gamma detector is reported in E. G. Hawman, "Non-rotating transaxial radionuclide imaging", U.S. Pat. No. 7,521,681 B2, Apr. 21, 2009, However, none of these include modeling and exploiting or measuring gamma radiation in a 3D measurement volume space that extends substantially along the radial direction. Therefore they have low sensitivity and the results are less reliable than the present invention. In prior art, SPECT/PET apparatus that measure gamma radiation at different angular positions tangential to a roughly circular contour around the object of interest is prevalent as the underlying theory for such apparatus is known to all persons skilled in the art. However, SPECT/PET apparatus that measure gamma radiation at different radial distances is not found anywhere except in the present invention. Such measurement along different radial distances was not considered in prior art perhaps because, based on intuition, it was assumed to provide no new information. There was no theoretical basis for such assumption as the new theory presented in here (Section 2.1, Eqs. 1.1 to 1.7) proves this assumption to be wrong.

Ohana et al (US 2010/0163736 A1) teaches a SPECT apparatus having a large collimator. However, Ohana et al's SPECT apparatus limits the motion of its gamma detector to orbit in a predetermined fixed radius orbit. The radius is fixed and the planar gamma detector moves tangentially to different angular positions similar to that shown in FIG. 3 here. The detector moves tangential to a roughly circular contour around the object of study but the detector does not move radially to different distances by moving farther and farther from the object of study. Therefore, the apparatus of Ohana et al does not capture essential information on the variation of gamma emission field along the radial direction that is needed for high-sensitivity 3D image reconstruction.

2.1 THEORETICAL BASIS OF THE PRESENT INVENTION

The insight and inspiration that lead to the present invention are two inventions for image deblurring and 3D shape-from-defocus techniques disclosed by this inventor in 1. M. Subbarao, "Methods and apparatus for computing the input and output signals of a linear shift-variant system", Jul. 7, 2009, U.S. Pat. No. 7,558,709.
2. M. Subbarao, "Direct Vision Sensor for 3D Computer Vision, Digital Imaging, and Digital Video", Aug. 18, 2009, U.S. Pat. No. 7,577,309.

The present invention is based on a new theory. It is based on measuring and inverting volume integrals instead of line integrals. Each photon detector element in the SPECT gamma detector measures the total emission from many or all the emission source elements in a certain 3D volume space. This 3D volume space could be, at one extreme, as large as the entire volume space in which the emission source is distributed, or, more typically, a portion of that entire volume space. At the other extreme, it could be the line integral as in a conventional SPECT theory.

Another fundamental difference between the new theory and the conventional SPECT theory is the following. Volume integrals must be measured in a 3D volume space that extends substantially along the radial direction pointing away from the emission source. Measuring on a thin surface that that is roughly perpendicular to the direction of emission rays as in the conventional SPECT theory is not adequate. For example, gamma emission from a source inside a human body may be measured in a 3D volume space in the shape of a thick annular cylinder (see FIG. 2), with an inner radius of 200 mm and an outer radius of 600 mm. Therefore, in the present invention, 3D volume integrals of spatial density distribution of the emission source are measured at a set of points spread out in a 3D volume space. This is unlike the conventional SPECT where 1D line integrals of spatial density distribution of the emission source are measured at a set of points spread out on a 2D surface (that is possibly curved as in the case of a thin annular cylinder).

Line integrals are a special case of volume integrals. In this sense the new theory is more general. In addition, it has practical advantages. The validity of the present invention has been verified through simple computer simulation experiments. A discrete source distribution was generated using a random number generator. The measured radiation field due to this distribution was computed at a discrete set of points by using a model of radiation propagation. This measured data was successfully inverted to obtain the original spatial distribution of the radiation source.

A theoretical proof of the validity of the present invention can be provided for a very simple case as follows. Consider a voxel array of size 100×100×100 mm^3 with a voxel size of 1×1×1 mm^3. Suppose that a radiation source is distributed in some portion of this space with intensity f(x,y,z), and the total incident radiation intensity is measured at all voxels in this space to obtain g(x',y',z'). Assume that the space is empty or vacuum except for the radiation source so that there is no attenuation of radiation. In this simple case, let h(x'−x,y'−y, z'−z) be the emission intensity measured at (x',y',z') due to a unit emission source located at (x,y,z). We obtain, due to conservation of energy as the radiation propagates to a radial distance of r from the source (one unit energy is distributed over a spherical surface of radius r having area $4\pi r^2$), $$h(x'-x, y'-y, z'-z) = 1/(4\pi r^2) \quad \text{(Eq. 1.1)}$$

where $$r^2 = (x'-x)^2 + (y'-y)^2 + (z'-z)^2, \quad \text{(Eq. 1.2)}$$

and $$g(x', y', z') = \sum_{x=1}^{100}\sum_{y=1}^{100}\sum_{z=1}^{100} h(x'-x, y'-y, z'-z)f(x, y, z). \quad \text{(Eq. 1.3)}$$

Above we have a 3D convolution relation. It can be denoted in the spatial domain by using '*' to denote the convolution operation as $$g = h * f \quad \text{(Eq. 1.4)}$$

and in the Fourier domain by a multiplication operation as $$G = HF \quad \text{(Eq. 1.5)}$$

where (g,G), (h,H), and (f,F) are Fourier transform pairs. Clearly the above equation can be easily inverted to solve for f by deconvolution as $$F = G/H \quad \text{(Eq. 1.6)}$$

and $$f = \text{Fourier Inverse of F}. \quad \text{(Eq. 1.7)}$$

The above proof is not a direct proof of the present invention, but strongly hints at the validity of the present invention. It shows that the gamma radiation field g measured as a volume integral at a set of discrete points in a 3D volume space which extends in all 3 dimensions contains information about the 3D spatial density distribution f of the radiation source. In general, this information about f that is contained in g cannot be erased by the presence of an attenuating medium such as the human body tissue in which the emission source is embedded. Information about f is lost only when attenuation is total and all radiation is blocked from leaving the body so that measured radiation everywhere outside the body is zero. This does not happen in nuclear medicine. Information may be "blurred" by noise and scattering, but not fully erased. By measuring the radiation g at a large number of points, an over-determined system of linear equations can be formulated and solved for f. By correcting for scatter and reducing the effect of noise, accurate and reliable results can be obtained.

As mentioned earlier, the present invention has been verified through simple computer simulation experiments with actual numerical examples.

The present invention is also useful in Positron Emission Tomography (PET). The novel method and apparatus for PET are similar to that of the novel SPECT method and apparatus. In the conventional PET apparatus, instead of collimators with small apertures, timing circuitry is used to detect coincident photon pairs emerging at 180 degrees apart. This expensive circuitry can be avoided in the novel method and apparatus for PET. All emitted photons are detected as in the novel SPECT and used in tomographic reconstruction.

In summary, the three-dimensional (3D) photon emission field measured with a very large aperture in a 3D volume space around an emission source can reveal the structure of the source distribution. By measuring the emission field in a 3D volume around the emission source, the 3D spatial density distribution of the emission source can be computed. Apparatus and method for achieving this are disclosed.

2.2 Detailed Theory: Deriving H and g=Hf+n

In this section additional details are provided on deriving a system matrix H and the equation g=Hf+n which is the basis of the method of the present invention. A gamma ray emission source S of unit intensity (power or energy per unit time, e.g. 1 watt) at a point (x,y,z) as in FIG. 6 produces an emission field of intensity $1/(4\pi r^2)$ (watts/meter sq.) at a distance of radius r from the source. This is due to the fact that the emitted 1 unit of power is uniformly distributed over a sphere with surface area $4\pi r^2$.

Figure 6:
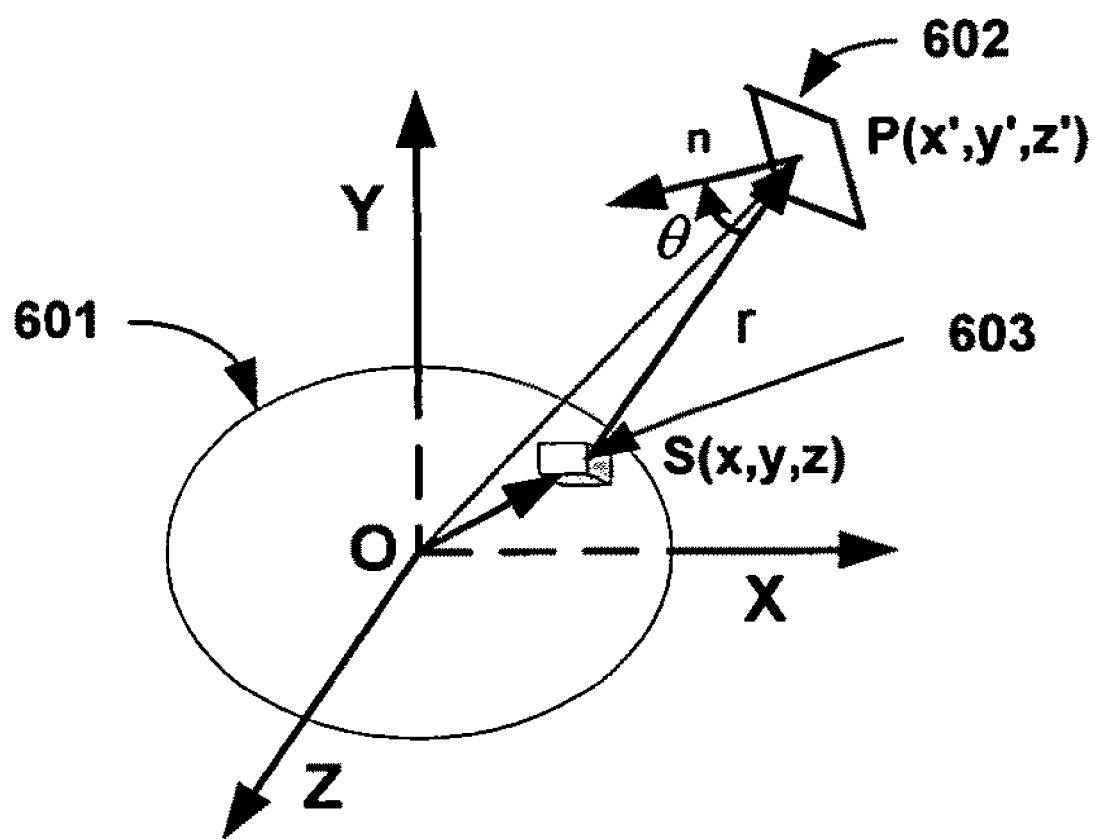

Let f(x,y,z) be the density (watts/meter cubed) of the radiation source at a point with coordinates (x,y,z) in a body. The radiation source element in a small volume element dv=dxdydz at (x,y,z) produces a gamma emission field at another point P(x',y',z) as shown in FIG. 6 given by $$f(x,y,z)dxdydz\ h(x'-x,y'-y,z'-z)\ \text{watts}/m^2 \quad \text{(Eq. 2.1)}$$

where $$h(x'-x,y'-y,z'-z)=1/(4\pi r^2) \quad \text{(Eq. 2.2)}$$

and $$r^2=(x'-x)^2+(y'-y)^2+(z'-z)^2. \quad \text{(Eq. 2.3)}$$

If this radiation source is present in empty vacuum, then the emission radiation intensity at the 3D point P(x',y',z) due to all of the source f(x,y,z) is the sum or integral of the field due to each of the volume element, given by:

$$g(x', y', z') = \iiint_V h(x' - x, y' - y, z' - z) f(x, y, z) dx\,dy\,dz \quad \text{(Eq. 2.4)}$$

If, as in FIG. 6, a small sensor element is placed at (x',y',z) with unit surface area dA and the surface normal is at an angle of θ(x',y',z',x,y,z) with respect to the direction of incidence of gamma emission from the source volume element at (x,y,z), then the measured radiation g(x',y',z') at (x',y',z) is $$g(x',y',z')=f(x,y,z)h(x'-x,y'-y,z'-z)dxdydz\ \cos(\theta(x',y',z',x,y,z))\ \text{watts}/m^2 \quad \text{(Eq. 2.4).}$$

If the known path attenuation coefficient due to the material substance of the emission ray as it traverses the path from (x,y,z) to (x',y',z) is C(x'y',z',x,y,z) then the measured radiation will be $$g(x',y',z')=f(x,y,z)h(x'-x,y'-y,z'-z)dxdydz\ \cos(\theta(x',y',z',x,y,z))C(x',y',z',x,y,z).w/m^2 \quad \text{(Eq. 2.5)}$$

(but the actual measured power by one sensor element is g(x',y',z') dA watts). If μ(x,y,z) is the linear attenuation coefficient at a point (x,y,z) in the body in which the emission source is embedded, then an estimate of C(x',y',z',x,y,z) is given by $$C(x', y', z', x, y, z) = \exp\left(-\int_{ray} \mu(r)dr\right) \quad \text{(Eq. 2.5.1)}$$

where the integral is a line integral along the emission ray that begins at (x,y,z) and ends at (x',y',z). The variable of integration r is along the ray and depends on (x',y',z',x,y,z). The linear attenuation coefficient μ(x,y,z) depends both on the energy spectrum of the photons and on the average atomic number of the material it passes through. This μ(x,y,z) is obtained by X-ray CT or MRI and then it is used to compute C(x',y',z',x,y,z) using the equation above (Eq. 2.5.1).

If there is no attenuation for all emitted rays due to absence of any attenuating material, then C(x',y',z',x,y,z)=1 for all (x',y',z',x,y,z).

If this emission is further attenuated by the collimator aperture geometry by a factor of a(x',y',z',x,y,z), then the measured radiation will be $$g(x',y',z')=f(x,y,z)h(x'-x,y'-y,z'-z)dxdydz\ \cos(\theta(x',y',z',x,y,z))C(x',y',z',x,y,z)a(x',y',z',x,y,z). \quad \text{(Eq. 2.6)}$$

Sometimes a(x',y',z',x,y,z) includes the factor cos(θ(x',y',z',x,y,z)) and in that case cos(θ(x',y',z',x,y,z)) factor can be dropped in the expression above.

If there is no collimator and therefore emissions from all points (x,y,z) reach the sensor at (x',y',z'), then a(x',y',z',x,y,z)=1 for all (x', y',z',x,y,z).

In the discrete domain let us define the system matrix H(x',y',z,x,y,z) as $$H(x',y',z',x,y,z)=h(x'-x,y'-y,z'-z)\ \cos(\theta(x'y',z',x,y,z))C(x',y',z',x,y,z)a(x',y',z',x,y,z). \quad \text{(Eq. 2.7).}$$

Therefore, the measured radiation field due to the presence of all radiation source elements distributed in the (x,y,z) space with density f(x,y,z) can be expressed in the discrete domain as $$g(x', y', z') = \sum_x \sum_y \sum_z H(x', y', z', x, y, z) f(x, y, z). \quad \text{(Eq. 2.8)}$$

In the equation above, unit volume was taken to be that of one voxel so that the term dxdydz=1. The summation is carried-out over all volume elements or voxels at points (x,y,z) where the radiation source may be present.

Due to noise and measurement errors together contributing n(x',y',z') to the above measured value above, we obtain:

$$g(x', y', z') = \sum_x \sum_y \sum_z H(x, y, z, x', y', z') f(x, y, z) + n(x', y', z') \quad \text{(Eq. 2.9)}$$

In this analysis we have so far ignored the effect of scattered radiation. Many techniques are available for estimating the scattered radiation and correcting for it. We assume that scattered radiation has been corrected by subtracting an estimate of scatter from g(x',y',z'). An estimate of scatter radiation is made through a known technique in prior art.

Let the radiation field g(x',y',z') be measured at a sufficiently large number of points (x',y',z') in a 3D volume space V in the vicinity of the radiation source. These points need not be in any regular pattern such as a grid. They need not even be contiguous or close. They could be distributed randomly. The minimum number of points is the minimum number of voxels in which the radiation source may be present. But these minimum number of points (x',y',z') must not be a degenerate set, e.g. they should not lie on a surface at constant radial distance. They must lie in a 3D volume space that extends substantially along the radial direction. Otherwise the equation above cannot be solved. In the case of non-degenerate set g(x',y',z'), the equation above can be expressed in vector matrix form using conventional notation as $$g = Hf + n \quad \text{(Eq. 2.10)}$$

Given measured values of g in a 3D volume space at a set of points (x',y',z'), it has been verified through simulation experiments that the equation above can be solved to obtain f. The effect of noise is reduced by using a suitable optimization method in the prior art.

3. DRAWBACKS OF PRIOR ART

Figure 4:
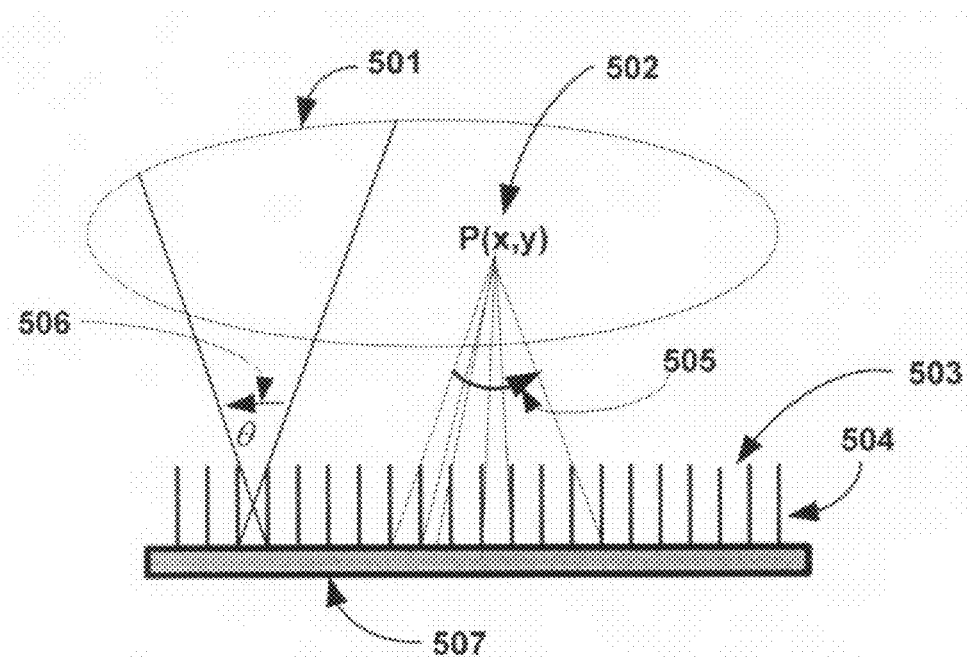

A fundamental drawback of prior art is the use of collimators with very narrow apertures (see FIG. 4). This typically discards more than 99 percent of information bearing gamma ray photons. As a result, signal to noise ratio is extremely low and in light of the present invention very unnecessary. SPECT apparatus in prior art aim to measure a line integral of the density of the emission source along the direction of view of the collimator. This is akin to using a pin-hole camera instead of a large aperture camera with a lens in consumer photography. Although there are no lenses to bend gamma rays in SPECT as the photons carry high energy, the present invention shows that there is a way around this problem.

An emission source in a small volume element emits its radiation equally in all directions, i.e. in a solid angle of $4\pi$ steradians or $(180/\pi)^2 = 3283$ square degrees. If a collimator lets only photons in 1 square degree solid angle, then only one out of every 3283 information bearing photons are recorded. The present invention can theoretically extract information from all the emitted photons with an increase in sensitivity of over 1000 times. However, in practice, it is estimated that an increase in sensitivity of 10 times or more is easily achieved. Using a larger collimator increases sensitivity, but it also "blurs" the image as a volume integral of the emission source is measured instead of a line integral. However, this blur is removed in the reconstructed 3D image of the emission source. This is made possible by measuring the radiation pattern in a 3D volume space that extends significantly along the radial direction in the vicinity of the radiation source instead of on a single 2D surface at different angles but at a nearly constant radial distance as in the SPECT apparatus of prior art (see FIG. 3).

In summary, SPECT apparatus in prior art use collimators with small apertures (FIG. 4) resulting in very low quality image data and low quality of image reconstruction. It also requires using a high dosage of radiopharmaceuticals resulting in harm to the patient as well as increased costs due to the need for larger amounts of radiopharmaceuticals being used per patient per SPECT scan. This is the biggest drawback that the present invention overcomes, by providing a very high-sensitivity SPECT apparatus and associated method with almost no increase in the cost of the apparatus. Similar advantages are provided in the novel PET method and apparatus. In addition, timing circuitry to determine coincident photons emitted in opposite directions will not be needed in the PET apparatus of the present invention.

4. OBJECTS AND ADVANTAGES OF THE INVENTION

It is an object of the present invention to provide a high-sensitivity SPECT method and apparatus that facilitates higher quality of reconstructed image in terms of the signal to noise ratio. Therefore the present invention provides a much more accurate clinical diagnosis of patients due to the more accurate reconstruction of 3D images of emission sources.

It is another object of the present invention to provide a safer SPECT imaging apparatus and method that uses a much lower dosage of radiophamaceuticals so that patients are exposed to lower ionizing radiation.

Another object of the present invention is to provide a cheaper a SPECT imaging method that uses lower dosage of radiopharmaceuticals and the cost of the radiopharmaceuticals per patient is reduced.

It is another object of the present invention to provide a high-sensitivity PET method and apparatus that facilitates more accurate, lower dosage, and cheaper PET imaging of patients. The requirement of timing circuitry for detecting coincident photons in opposite directions is avoided.

An advantage of the present invention is a high-sensitivity apparatus for use in medical imaging, particularly SPECT imaging, wherein a large aperture collimator is used to admit more gamma rays to strike the photon detector, thus increasing sensitivity by a factor, of at least 5 and likely much more than 10.

Another advantage of the present invention is a nuclear medical imaging device that uses much less dosage of radiopharmaceuticals on patients thus reducing harm to the patients. Reduced dosage will be adequate for SPECT imaging due to the increased sensitivity of the SPECT apparatus.

A further advantage of the present invention is a reduction in the cost of each SPECT/PET scanning procedure by reducing the amount of dosage of radiopharmaceuticals on patients. Reduced dosage will be adequate for SPECT/PET imaging due to the increased sensitivity of the apparatus.

Further advantages of the present invention will become apparent hereinafter to those with ordinary skill in the art to which the present invention pertains.

5. BRIEF DESCRIPTION OF THE DRAWINGS

Partial List of Reference Numerals in the Drawings

FIG. 1: 101, 102, 103, 104: 2D GAMMA RAY DETECTOR
- 105: OBJECT SCANNED
- 106: RADIATION SOURCE

Figure 2:
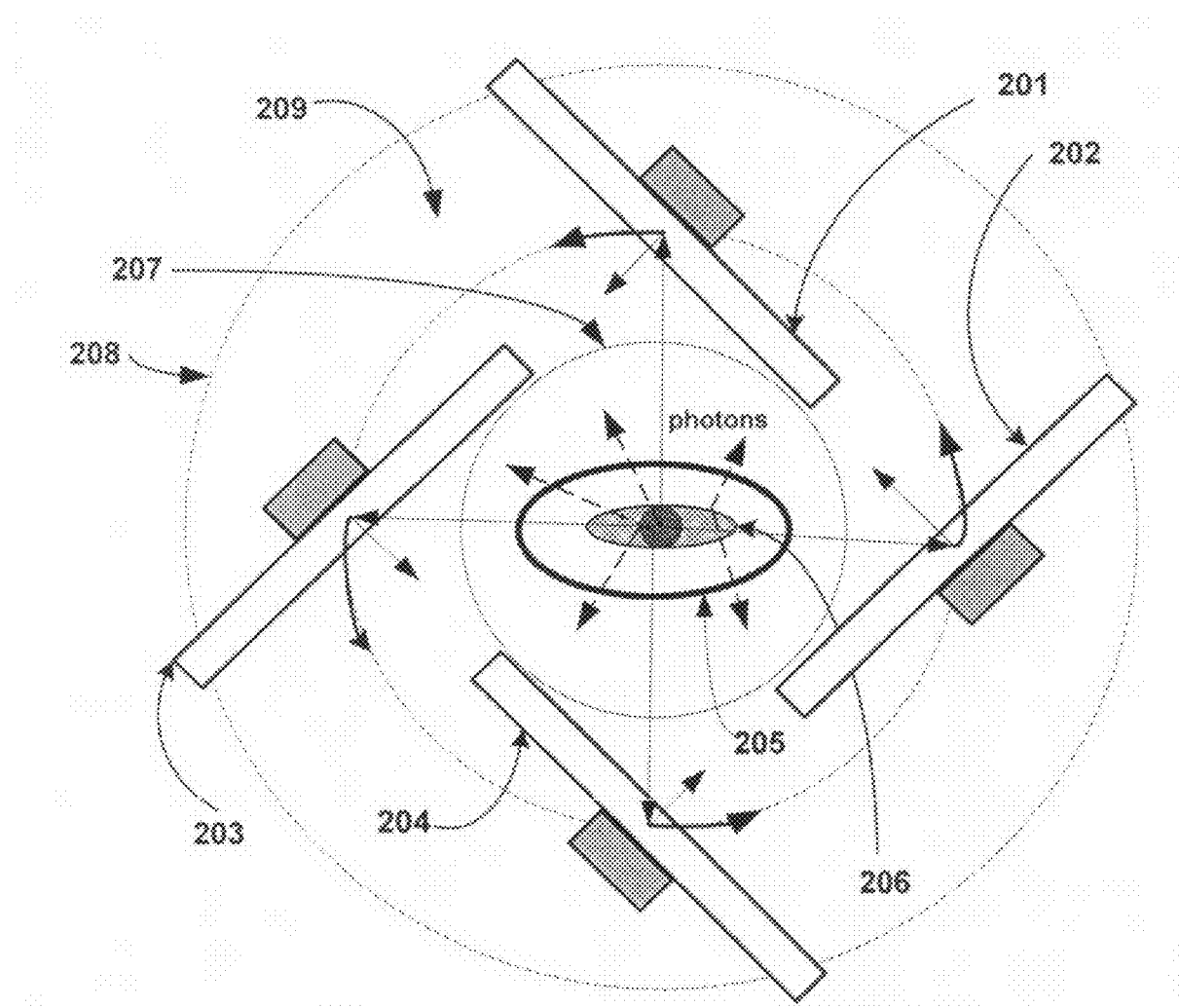

FIG. 2: 201, 202, 203, 204: GAMMA RAY DETECTOR,
- 205: OBJECT SCANNED
- 206: RADIATION SOURCE,
- 207: INNER CYLINDER OF VOLUME SPACE,
- 208: OUTER CYLINDER OF VOLUME SPACE
- 209: 3D VOLUME SPACE WHERE GAMMA RADIATION IS MEASURED

FIG. 3: 401: GAMMA RAY DETECTOR,
- 402: RADIATION SOURCE
- 403: OBJECT SCANNED

Figure 5:
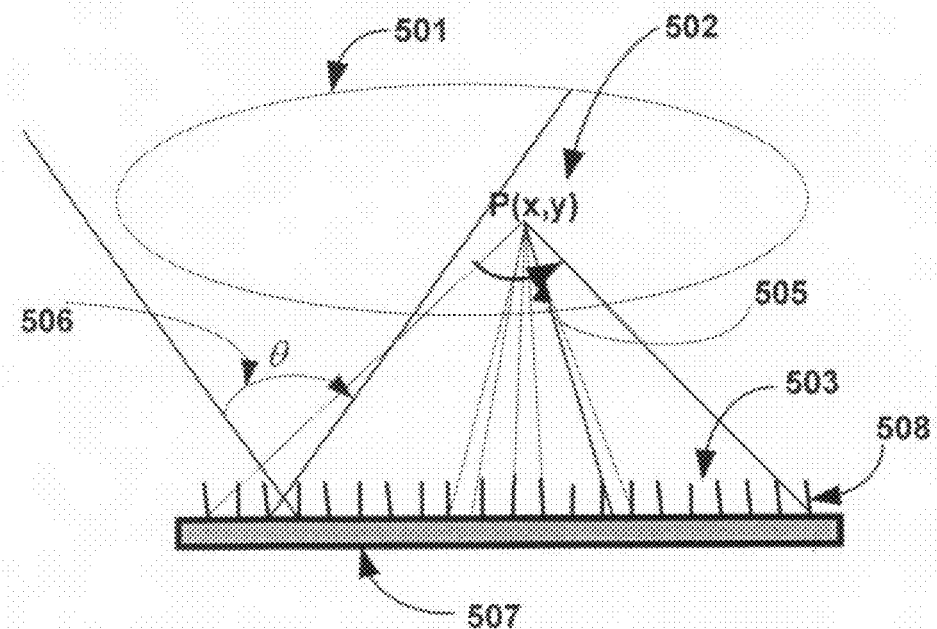

FIG. 4, FIG. 5:
- 501: OBJECT OF STUDY,
- 502: EMISSION SOURCE
- 503: COLLIMATOR APERTURE
- 504: LONG COLLIMATOR
- 505: SENSITIVITY ANGLE
- 506: COLLIMATOR FIELD OF VIEW
- 507: 2D GAMMA RAY DETECTOR
- 508: SHORT COLLIMATOR

FIG. 6: 601: OBJECT OF STUDY
- 602: GAMMA DETECTOR ELEMENT
- 603: VOLUME ELEMENT OF EMISSION SOURCE

FIG. 1 shows a cross-section of a novel SPECT apparatus. It illustrates a target object 105 with radiopharmaceutical 106 embedded in it. Object 105 is scanned in a 3D volume around it. Four 2D planar gamma ray detectors 101, 102, 103, and 104, are placed at top, right, left, and bottom respectively of the object with the detector surface facing the object. These detectors are moved to different distances from the object along paths like 107, and at each distance, one gamma ray image is captured. The collection of all such images constitutes a discrete sampling g of the gamma ray field in a 3D volume space around the object.

FIG. 2 shows a cross-section of another embodiment of the novel SPECT apparatus. It illustrates four 2D gamma ray detectors 201, 202, 203, and 204, at an angle from the direction of radiation. These detectors are rotated around the object 205 of study to different positions with the detector surface always facing the object at a non-perpendicular angle such as 45 degrees. This non-perpendicular structure helps in measuring the gamma field along the radial dimension in a 3D volume space around the emission source 206. At each position one gamma ray image is captured. The collection of all such images together constitutes a discretely sampled measurement g of the gamma emission field in a 3D volume around the object of study. In this embodiment images may be captured at 3 degree intervals by rotating the detectors by a total of 90 degrees.

Figure 3:
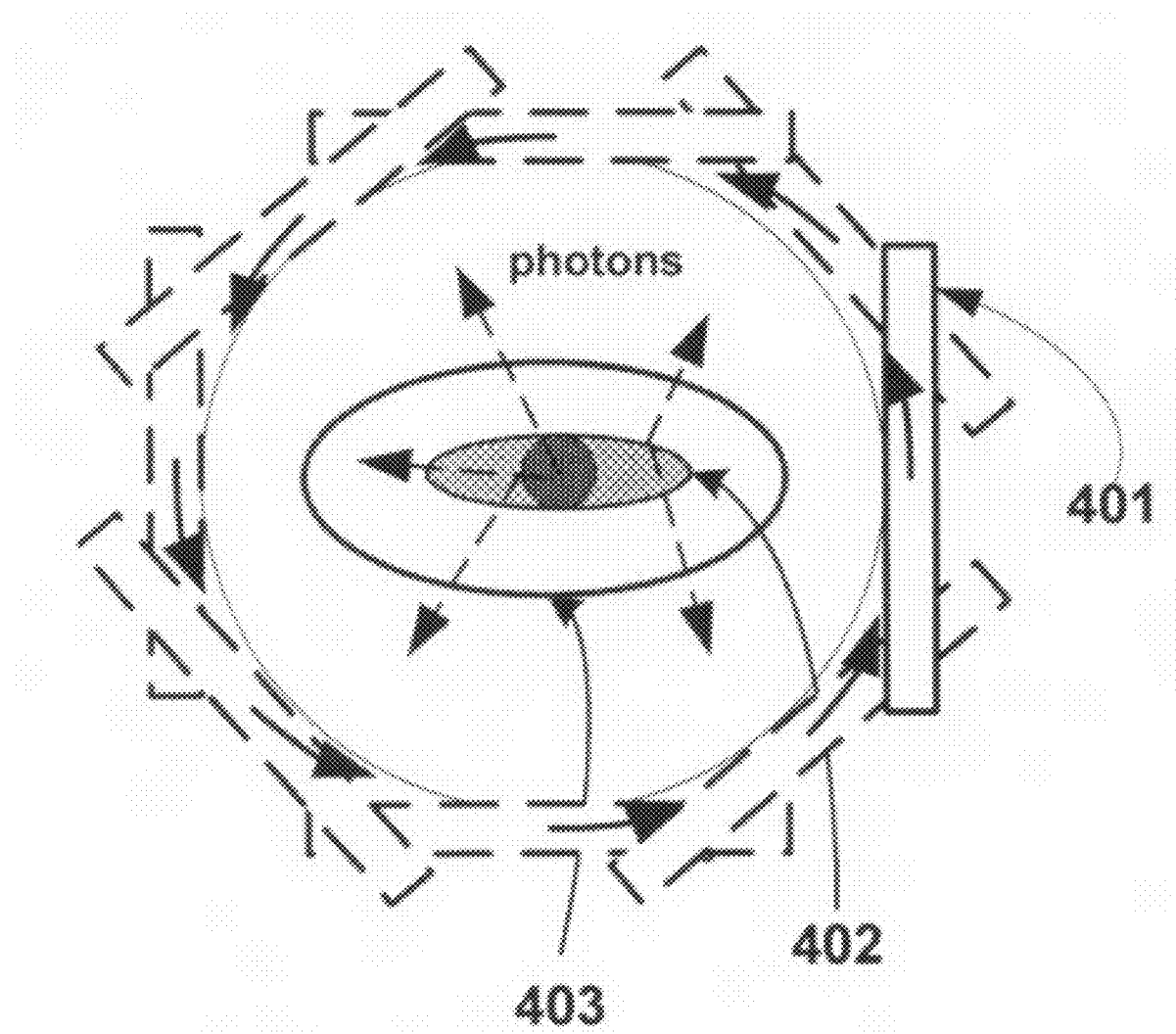

FIG. 3 shows a cross-section of a 3D object 403 containing a gamma ray emission source 402 being imaged by a conventional SPECT apparatus. It includes a 2D gamma detector array 401 that is rotated around the object in a circle of almost constant radius. Detector surface is perpendicular to the emission from the object center. Images are captured at regular intervals of around 1 to 5 degrees. 3D volume space covered by the gamma detectors is very thin along the radial direction. Collimators with small aperture or field-of-view are used and therefore sensitivity is low.

FIG. 4 shows a cross-section of a gamma detector array in a conventional SPECT apparatus. The collimators of the gamma detectors have a very small aperture or a small field-of-view (1 degree to 5 degrees) and therefore low sensitivity. Typical aperture diameter is 1 mm and collimator length is 20 mm which provides a 3 degrees field of view. About 99% of information bearing photons are blocked by the collimator walls from reaching the detector and therefore wasted.

FIG. 5 shows a cross-section of a gamma detector array in a novel SPECT apparatus of the present invention. The collimators of the gamma detectors have a very large aperture or a large field-of-view (5 degree to 20 degrees) and therefore have high sensitivity. Typical aperture diameter is 1 mm and collimator length is 0 to 5 mm which provides around 15 degrees or larger field of view. Sensitivity is increased by a factor of at least 5 but typically over 10.

FIG. 6 shows the geometry of emission radiation from a small volume element S at (x,y,z) sensed by a gamma detector pixel P at (x',y',z). It also shows the surface normal vector n of the pixel and the angle of incidence $\theta$ between this surface normal and the emitted radiation along SP. The distance between the source element S and detector pixel P is r. This geometry is used to compute the system matrix H described later.

FIG. 7 shows a flow-chart of the method of the present invention.

6. BRIEF SUMMARY OF THE INVENTION

A high-sensitivity Single-Photon Emission Computed Tomography (SPECT) apparatus and method are disclosed. A very similar apparatus and method are useful in Positron Emission Tomography (PET). The SPECT apparatus comprises a gamma ray detector with an array of sensor elements or pixels. Each pixel of the detector array is provided with a substantially large collimator aperture of at least 5 degrees field of view and up to 180 degree field of view. This enhances detection sensitivity significantly by measuring a volume integral of gamma ray emission from an emission source distributed in a large 3D volume space instead of a line integral corresponding to just a small volume space such as along a thin line-like space. This detector array is provided with the following capabilities.

1. It can move to different spatial positions to sweep or cover a three-dimensional (3D) measurement volume space in a vicinity of a source of gamma ray emission radiation. This source is the object of study whose spatial density distribution is to be estimated. In particular, the 3D volume space in which the detector moves extends significantly along at least one radial direction pointing away from an approximate center point of the radiation source. The 3D measurement volume space in particular must have an essential feature of extending very substantially and significantly along at least one radial direction pointing away from an approximate center point of the radiation source. This feature provides a means for measuring gamma radiation field at different radial distances from the radiation source.
2. It can measure the gamma radiation at each spatial position where the detector array moves.
3. It can provide a set of discretely sampled measured values of the gamma radiation field of the emission source in the vicinity of the source in the 3D measurement volume space.

The 3D volume space where the detector array moves can extend significantly in all three spatial dimensions (x,y,z). It can also be a thin volume slice parallel to a plane extending along at least one radial direction pointing away from an approximate center point of the radiation source.

The gamma ray detector can be a planar detector that is moved to different radial distances that is along a direction pointing away from an approximate center point of the source, and to different angular positions, to sweep a 3D volume space. The gamma ray detector can also be a planar detector that significantly deviates from being perpendicular by 5 degrees to 89 degrees with respect to the direction of gamma ray emission from an approximate center of the gamma ray source, and capable of moving or rotating to different angular directions of up to 360 degrees to sweep the 3D volume space. In another embodiment, the gamma ray detector array can be a plurality of planar detectors configured at different angles.

The apparatus can be provided with an integrated X-ray or an MRI (Magnetic Resonance Imaging) computed tomography apparatus for determining gamma ray attenuation coefficients of material in which the gamma ray emission source is embedded.

The gamma detector of the apparatus can be built to detect photons for SPECT imaging where the photons have energy in the range of 10 to 400 keV or it can be built to detect photons with energy in any other range, including specifically the photons in Positron Emission Tomography (PET) where the photons have an energy of around 511 keV. Therefore the present invention provides apparatus for both PET and SPECT. In the PET apparatus, there will be no need for the timing circuitry to detect coincident photons emitted in opposite directions. Therefore, cost of the apparatus is reduced.

The present invention discloses a method of determining the spatial density distribution of a gamma ray emission source such as a radiopharmaceutical substance in SPECT and PET applications. In this case, the emission source is embedded in a body and emitting gamma rays. The method comprises the following steps.

1. Measuring a discretely sampled vector of values g using a gamma ray detector of gamma radiation field of the emission source in a vicinity of the source in a 3D volume space. This 3D volume space is comprised of a set of volume elements or voxels represented by a 3D matrix V, and it extends significantly along at least one radial direction pointing away from an approximate center of the radiation source.
2. Measuring an attenuation coefficient matrix $\mu(x,y,z)$ of the material present in a portion of volume P of the body at different volume elements or voxels through which the gamma radiation passes through before being measured in step (1). The portion of volume P includes a set of voxels S in which the radiation source is embedded. $\mu(x,y,z)$ is used to compute a gamma ray path attenuation coefficient matrix $C=c(x',y',z',x,y,z)$ that provides the attenuation of a gamma ray going from point $(x,y,z)$ to $(x',y',z')$,
3. Determining a system matrix H of values using
   (a) the distance and geometry between pairs of voxels (v,s) where v is a voxel in V and s is a voxel in S, and the geometry and sensor characteristics of the gamma ray detector,
   (b) the path attenuation coefficient matrix C,
   (c) the property of radiation propagation that the intensity per unit area of gamma ray emission field decreases with the square of radial distance from emission source; this facilitates the use of data values in g measured at different radial distances from the emission source, and
   (d) a discrete vector n of values that represents the effects of noise and scattered radiation on measurements in step (a) and (b) above, so that the relation between a discretely sampled vector of values f representing the spatial density distribution of the radiation source that needs to be determined in voxles S is given by $g=Hf+n$; and
4. solving the above equation $g=Hf+n$ for the desired quantity f by a method that reduces the effect of noise n significantly so that the desired goal of determining the spatial density distribution f of the radiation source is achieved.

In this method, Step (4) of solving for f can be based on any one of the following approaches (a) a Singular-Value decomposition of H and spectral filtering or regularization, (b) maximizing the probability of observing g given f to be the spatial density distribution of the radiation source, and (c) an iterative algebraic reconstruction technique. In each of these cases, Step (4) of solving for f can use the positivity constraint that all components of f are non-negative, i.e. zero or more.

The measurement of gamma ray attenuation coefficient matrix $\mu(x,y,z)$ in step (2) can be made either by an X-ray computed tomography method or MRI method. The discretely sampled vector of values g can represent a gamma radiation intensity due to a conventional SPECT process or a PET process. In all cases, the discretely sampled vector of values g can be first corrected for an estimated scattered radiation intensity before processing it further.

7. DETAILED DESCRIPTION OF THE INVENTION

7.1 Apparatus of the Invention

A high-sensitivity Single-Photon Emission Computed Tomography (SPECT) apparatus includes a two-dimensional (2D) gamma detector array. This is typically a planar photon sensitive array of elements that are collimated. A cross section of such an array is shown in FIG. 5 with parallel-hole collimators, but collimators with other geometries such as converging/diverging holes, fan-beam, and cone-beam arrangements can also be used. In addition, unlike a conventional SPECT machine, each photon detector element or pixel in the 2D gamma detector array is provided with a very large collimator aperture corresponding to a field of view of 5 degrees to 180 degrees. See FIG. 4 and FIG. 5. This increases the sensitivity of the novel SPECT apparatus by a factor of at least 5 and often by over 20 in comparison with a conventional SPECT machine. The photon sensitive detector elements can be sensitive to gamma photons with different energies including photons emitted in SPECT (10-400 KeV) as well as PET (511 KeV range). The apparatus of the present invention can be used for both SPECT and PET. In the case of PET, timing circuitry for detecting coincident photons (511 KeV) in opposite directions (180 degrees) will not be necessary.

One or more of planar gamma detector arrays are used to measure gamma emission radiation in a three-dimensional (3D) volume space in the vicinity of an emission source of interest. FIG. 1 shows a cross-section of one embodiment in which four 2D planar gamma detectors—101, 102, 103, and 104,—are placed around an object such as a patient's body 105. A radionuclide gamma emission source 106 is embedded in this object.

Measuring the 3D spatial density distribution f of the emission source is the purpose of this apparatus. The 2D planar gamma detectors are placed at 90 degrees apart at left, right, top, and bottom, with respect to the body. The gamma detector at the top 101 and bottom 104 are moved to different distances from the object 105 that are about a few millimeters apart, and at each distance the gamma detectors capture images. Similarly, the left and right gamma detectors are moved to different distances from the body while facing the body, and at each distance gamma images are captured. Each of the 4 gamma detectors measure the gamma emission field in a 3D volume in the shape of a cuboid. The inner and outer faces of the cuboid has the same shape as the planar detector and its length is equal to the distance by which detector moves from the closest point to the farthest point of the object. The image data captured by all the 4 planar detectors together constitutes g which is a measurement of the gamma field in a 3D volume space around the object being scanned. In particular, unlike conventional SPECT apparatus, this 3D volume space extends substantially along the radial direction pointing away from an approximate center of the emission source.

Another variation of the embodiment can use a single planar gamma detector that moves to at least one but possibly all the four different positions of top, bottom, left, and right in sequence, and captures a 3D gamma image g by moving to different distances from the object. In another embodiment, a pair of gamma detectors, say top and bottom, are used to make a similar measurement of g in two steps by moving to two angular positions that are 90 degrees apart. In another embodiment one or more detectors move to more than 4 angular positions at regular intervals of less than 90 degrees such as 45 degrees and measure g.

In the apparatus shown in FIG. 1, the 3D volume space in which g is measured extends significantly in all three spatial dimensions of (x,y,z) Cartesian coordinates. The present invention is also applicable to the case where g is measured in a thin volume slice that extends by a small amount along one axis, say z, but substantially along the other two axes (x,y) so that the x-y plane contains a radial direction. In this case, the collimator apertures have a very narrow field of view with respect to the z-axis as in FIG. 4, but have a wide field of view in the perpendicular direction as shown in FIG. 5. In this embodiment, the body being scanned is placed longitudinally along the z-axis. Gamma images of thin slices perpendicular to the z-axis of the body are captured and processed. In this case, the gamma detectors measure an area integral as opposed to a line integral in a conventional SPECT apparatus, or a volume integral in the previous embodiment of the present invention.

The present invention includes apparatus and method for measuring not only area or 2D integrals and volume or 3D integrals as opposed to line or 1D integral in a conventional SPECT apparatus, but it also includes measuring and processing 4D integrals in space-time dimensions (x,y,z,t) wherein video image data g is captured instead of instantaneous image data. Video data provides dynamic information about the body being scanned, e.g. a contracting/expanding heart.

Another embodiment of the present invention is shown in FIG. 2. It includes four planar gamma detectors 201, 202, 203, and 204, similar to those in FIG. 1, but the detectors are placed so that they are not perpendicular but at an angle of 5 to 85 degrees from the radial direction. In FIG. 2, the detectors are shown to be at about 45 degrees with respect to the radial direction. The four detectors are placed roughly 90 degrees apart around the body 205 to be scanned. The body contains a gamma emission source 206 embedded in it. These detectors are rotated to different angular positions that are a few degrees apart, say 3 degrees to 10 degrees, by a total of 90 degrees rotation. At each angular position, the detectors capture gamma images to obtain the image data g. In this embodiment, as described in the case of a previous embodiment, the collimator holes can be parallel, converging/diverging, and fan/cone-beam. The collimators can also have large field of view in one direction but small field of view in the perpendicular direction so that area integrals of gamma emission from thin volume slices could be measured. Further, alternative embodiments may contain different numbers of gamma detectors instead of four shown in FIG. 2. Only one detector can be rotated by 360 degrees or less, two detectors at opposite ends may be rotated by 180 degrees or less, etc.

In another embodiment of the present invention, the SPECT apparatus of the present invention includes an X-ray computed tomography apparatus integrated with it for determining the gamma ray attenuation coefficients of the material in which the gamma ray emission source is embedded.

In another embodiment of the present invention, the SPECT apparatus of the present invention includes a Magnetic Resonance Imaging (MRI) tomography apparatus integrated with it for determining the gamma ray attenuation coefficients of the material in which the gamma ray emission source is embedded.

7.2 Method of the Invention

FIG. 7 shows a flow chart of the method of the present invention. It is a method of determining the spatial density distribution in a body of a radiopharmaceutical substance or emission source radiating gamma rays. The body containing the emission source is scanned by a SPECT apparatus of the present invention.

STEP 1: In the first step, a discretely sampled vector of values $g=g(x',y',z')$ is measured using a gamma ray detector. This g is a measure of the intensity of the gamma radiation field of the emission source in a vicinity of the source. It is measured in a 3D volume space comprised of a set of volume elements or voxels represented by a matrix V. The 3D volume space should extend significantly along at least one radial direction pointing away from the approximate center of the radiation source.

STEP 2: In the next step of the method, a discretely sampled matrix of values $\mu(x,y,z)$ is measured. This $\mu(x,y,z)$ represents the gamma ray attenuation coefficients of the material in which the radiation source is embedded and through which it passes through. $\mu(x,y,z)$ is measured in a portion of volume P of the body or object of study at different volume elements or voxels through which gamma radiation passes through before being measured in step (1) above. The portion of volume P should include the set of voxels S in which the radiation source is embedded. MRI or X-ray CT may be used for estimating $\mu(x,y,z)$. Using this $\mu(x,y,z)$ and Eq. (2.5.1), compute a path attenuation coefficient matrix $C=c(x',y',z',x,y,z)$ that gives the total attenuation of an emission ray going from point $(x,y,z)$ to the sensor detector at $(x',y',z')$. This step involves computing the line integral of the attenuation coefficients along the path traversed by emitted rays.

STEP 3: Next the system matrix H that characterizes the SPECT apparatus and radiation propagation is computed as follows. The distance r between pairs of voxels (v,s) where v is a voxel in V at $(x',y',z')$ and s is a voxel in S at $(x,y,z)$ is determined. See FIG. 6. A gamma photon sensor element or a pixel located at v receives gamma emission radiation from a source element located at voxel s. The amount of radiation received depends on the distance r, and the angle a between the surface normal n of the sensor pixel and the direction of the incident ray from s to v. The geometry of the collimator aperture and sensor characteristics of the gamma ray detector also affect the measured radiation at a pixel. The effect of the aperture geometry of the collimator can be expressed by a function of the form $a(x,y,z,x',y',z')$. See earlier sections for more details. The attenuation path attenuation coefficient matrix $C=c(x',y',z',x,y,z)$ is also used in computing H. The property of radiation propagation given by (Eq. 1.1) and (Eq. 1.2) and characterized by $h(x'-x,y'-y,z'-z)$ that the intensity per unit area of gamma ray emission field decreases with the square of radial distance from emission source is also used. H is then computed using Eq. (2.7) as $$H(x',y',z',x,y,z)=h(x-x',y'-z'-z)\cos\theta(x,y,z,x'y'z')C(x,y,z,x'y'z')a(x,y,z,x'y'z')$$

STEP 4: A discrete vector n of values that represents the effects of noise and scattered radiation on measurements in step (1) and (2) above is estimated. The relation between a discretely sampled vector of values f representing the spatial density distribution of the radiation source that needs to be determined in voxles S, is given then by g=Hf+n.

STEP 5: This equation g=Hf+n is then solved for the desired quantity f by a method that reduces the effect of noise significantly so that the desired goal of determining the spatial density distribution f of the radiation source is achieved. The matrix H is typically very large and the measured gamma ray values in vector g are noisy. Therefore different optimization techniques and statistical techniques are used for solving the equation g=Hf+n to determine the 3D spatial distribution f of the emission source.

One method of solving g=Hf+n for f is based on the well-known classical technique of spectral filtering based on Singular Value Decomposition (SVD) of H and regularization. The singular values of H are computed, filtered suitably to reduce the effect of noise and incorporate regularization to obtain a smooth solution, and the results are used to compute f.

Classical statistical optimization methods can also be used to solve g=Hf+n for f. On example is to maximize the probability of observing g given f to be the spatial density distribution of said radiation source.

Another method of solving g=Hf+n for f is the well-known iterative algebraic reconstruction technique with several variations.

In this method, the measurement of $\mu(x,y,z)$ in Step (2) can be made by X-ray computed tomography, or a Magnetic Resonance Imaging (MRI) technique.

The method of solving for f is improved by using the positivity constraint that all components of f must be non-negative, i.e. zero or more.

The method of the present invention is also applicable to Positron Emission Tomography (PET) where a radionuclide decays and emits a positron. The discretely sampled vector of values g can represent a gamma radiation intensity induced by the annihilation of the positron and an electron. Such annihilation produces two gamma photons with about 511 keV energy each in opposite directions at 180 degree angle. However, in the present method, it will not be necessary to use timing circuitry to detect coincident photons that are emitted 180 degrees apart. All photons that pass through the wide field-of-view collimators, at anytime (not necessarily coincident in time) are detected and counted, regardless of whether there was a corresponding photon that was incident at the same time in the opposite direction. This reduces the cost of the PET apparatus that can be used in the present method. Simple photon radiation intensity is recorded and processed, just as in the case of SPECT method The present method is improved by adjusting the value of the discretely sampled vector g by first estimating the intensity of scattered radiation and subtracting this estimate from g. The resulting corrected g is used in solving the equation g=Hf+n for f.

8. CONCLUSION, RAMIFICATIONS AND SCOPE OF THE INVENTION

While the description in this report of the method, apparatus, and applications contains many specificities, these should not be construed as limitations on the scope of the invention, but rather as exemplifications of preferred embodiments thereof. Further modifications and extensions of the present invention herein disclosed will occur to persons skilled in the art to which the present invention pertains, and all such modifications are deemed to be within the scope and spirit of the present invention as defined by the appended claims and their legal equivalents thereof.

What is claimed is:

1. A method of determining the spatial density distribution of a gamma ray emission source such as a radiopharmaceutical substance, said emission source embedded in a body and emitting gamma rays, and said method comprising the steps of:
   (a) measuring a discretely sampled vector of values g using a gamma ray detector of gamma radiation field of said emission source in a vicinity of said source in a 3D volume space comprised of a set of volume elements or voxels represented by a 3D matrix V, said 3D volume space extending significantly along at least one radial direction pointing away from an approximate center of said radiation source;
   (b) measuring an attenuation coefficient matrix $\mu(x,y,z)$ of material present in a portion of volume P of said body at different volume elements or voxels through which gamma radiation passes through before being measured in step (a), wherein said portion of volume P includes a set of voxels S in which said radiation source is embedded, and, using $\mu(x,y,z)$ to compute a gamma ray path attenuation coefficient matrix C=c(x',y',z',x,y,z) that provides the attenuation of a gamma ray going from point (x,y,z) to (x',y',z'),
   (c) determining a matrix H of values using
      (i) the distance and geometry between pairs of voxels (v,s) where v is a voxel in V and s is a voxel in S, and the geometry and sensor characteristics of said gamma ray detector,
      (ii) the path attenuation coefficient matrix C,
      (iii) the property of radiation propagation that the intensity per unit area of gamma ray emission field decreases with the square of radial distance from emission source, and therefore facilitating the use of data values in g measured at different radial distances from said emission source, and
      (iv) a discrete vector n of values that represents the effects of noise and scattered radiation on measurements in step (a) and (b) above, so that the relation between a discretely sampled vector of values f representing the spatial density distribution of said radiation source that needs to be determined in voxels S is given by g=Hf+n; and
   (d) solving the above equation g=Hf+n for the desired quantity f by a method that reduces the effect of noise n significantly so that the desired goal of determining the spatial density distribution f of said radiation source is achieved.

2. The method of claim 1 wherein said method in Step (d) of solving for f is based on a Singular-Value decomposition of H and spectral filtering or regularization.

3. The method of claim 1 wherein said method in Step (d) of solving for f is based on maximizing the probability of observing g given f to be the spatial density distribution of said radiation source.

4. The method of claim 1 wherein the measurement of gamma ray attenuation coefficient matrix $\mu(x,y,z)$ in step (b) is made by X-ray computed tomography.

5. The method of claim 1 wherein the measurement of gamma ray attenuation coefficient matrix $\mu(x,y,z)$ in step (b) is made by Magnetic Resonance Imaging.

6. The method of claim 1 wherein said method in Step (d) of solving for f is based on an iterative algebraic reconstruction technique.

7. The method of claim 1 wherein said method in Step (d) of solving for f uses the positivity constraint that all components of f are non-negative, i.e. zero or more.

8. The method of claim 1 wherein said discretely sampled vector of values g represent a gamma radiation intensity due to a Single-Photon emission process as in a conventional SPECT method.

9. The method of claim 1 wherein said discretely sampled 1 vector of values g represent a gamma radiation intensity due to a positron-emission process wherein an emitted positron is annihilated by an electron to produce a pair of photons in opposite directions along a line as in a conventional PET process.

10. The method of claim 1 wherein said discretely sampled vector of values g is first corrected for an estimated scattered radiation intensity before processing it further.

* * * * *